United States Patent [19]

Tabushi et al.

[11] 4,168,265
[45] Sep. 18, 1979

[54] ALKYL SUBSTITUTED CYCLAMS

[75] Inventors: Iwao Tabushi; Mariko Fujiyoshi, both of Kyoto; Hidefumi Kato, Kurume; Yasuhisa Kuroda, Osaka, all of Japan

[73] Assignee: Iwao Tabushi, Kyoto, Japan

[21] Appl. No.: 874,935

[22] Filed: Feb. 3, 1978

[30] Foreign Application Priority Data

May 19, 1977 [JP] Japan .................................. 52-57124

[51] Int. Cl.$^2$ ........................................... C07D 245/02
[52] U.S. Cl. ............................. 260/239 BC; 252/184
[58] Field of Search ................................. 260/239 BC

[56] References Cited

U.S. PATENT DOCUMENTS

| B 403,326 | 1/1976 | Richman ...................... 260/239 BC |
| 3,828,023 | 8/1974 | Cormer et al. .................. 260/239 BC |
| 3,860,576 | 1/1975 | Ham et al. ..................... 260/239 BC |

Primary Examiner—Donald G. Daus
Assistant Examiner—D. B. Springer
Attorney, Agent, or Firm—Frishauf, Holtz, Goodman & Woodward

[57] ABSTRACT

Alkyl cyclam resulting from substitution of one or more hydrogens of the cyclam represented by the formula

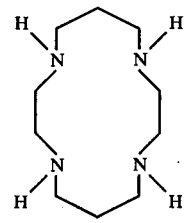

by alkyl groups containing at least 8 carbon atoms.

The alkyl cyclam can be used for capturing metal ions.

7 Claims, No Drawings

ALKYL SUBSTITUTED CYCLAMS

BACKGROUND OF THE INVENTION

1. Field of the Invention

The present invention relates to novel compounds. More particularly it is concerned with alkyl cyclam which can be used in selectively and efficiently capturing metal ions, for example, metal ions contained in waste water.

2. Description of the Prior Art

Metal ions such as copper, cobalt, nickel, mercury, cadmium, zinc and the like ions contained in waste water have hitherto been removed from the standpoint of preventing pollution. Metal ion capturing agents for use in removing these metal ions include activated carbon, kieselguhr, and the like, which capture the metal ions by the physical absorption action, and ion exchange resins, chelate resins, and the like, which capture the metal ions by the chemical binding action. These metal ions capturing agents, however, are of no practical value since activated carbon, kieselguhr, and the like are insufficient in removing low concentrations of the metal ions, and ion exchange resins are of low selectivity to the metal ions. With regard to chelate resins, since they are of high selectivity to all the heavy metal ions, they are suitable for use in removing all the heavy metal ions from industrial waste water for preventing pollution. These chelate resins, however, have a disadvantage in that since they are of low selectivity to specific metal ions, they cannot be employed in selectively separating, purifying and concentrating a specific metal ion from the metal ion mixture in which various kinds of metal ions coexist, for example, in recovery of noble metal and the like.

As a method of separating or concentrating uranium from an aqueous solution containing uranium, a solvent extraction method using amines is known. This procedure, however, is markedly disadvantageous from a practical standpoint since it requires a large amount of amines because of its low ability to form a complex with uranium.

Thus it has long been desired to develop novel materials capable of selectively and effectively capturing metal ions. We have found that cyclam (i.e. 1,4,8,11-tetraazacyclotetradecane) forms a stable complex compound with copper ion in an aqueous solution. Further, we found that a novel compound resulting from the substitution of one or more hydrogens of the cyclam by alkyl groups has an excellent ability to capture metal ions selectively.

SUMMARY OF THE INVENTION

The present invention provides a novel alkyl cyclam, that is alkyl-substituted cyclam (i.e. 1,4,8,11-tetraazacyclotetradecane). One or more alkyl groups containing at least 8 carbon atoms are introduced into the cyclam. This compound can be used as a capturing agent for metal ions.

DETAILED DESCRIPTION OF THIS INVENTION

Alkyl cyclam of this invention results from the substitution of one or more hydrogens of the cyclam represented by the formula

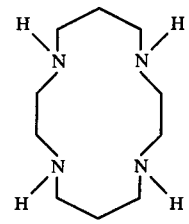

by alkyl groups containing at least 8 carbon atoms.

The hydrogens of the skelton represented by the above general formula to be substituted with alkyl substituents may be either those hydrogens bonded to the ring nitrogen atoms or those hydrogens bonded to the ring carbon atoms or both of them.

The number of the alkyl groups to be introduced is not subjected to any special limitation. From one to all of the ring hydrogens may be substituted with alkyl groups. The alkyl groups being used should be those containing at least 8 carbon atoms. In general, those alkyl groups containing 8 to 20 carbon atoms are preferred. Those alkyl substituted cyclams with alkyl group containing 7 or less carbon atoms introduced thereinto are of high solubility in water and are difficult to separate as oil layers, and thus they are not suitable for use in capturing metal ions.

Examples of the alkyl cyclam of the present invention are shown as follows:

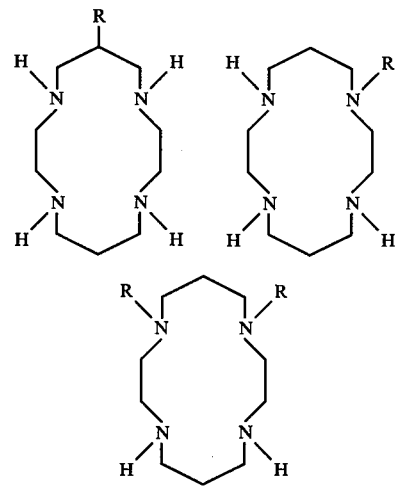

wherein R is alkyl group containing from 8 to 20 carbon atoms.

Preferred examples of the alkyl cyclam of the present invention are those compounds represented by the following formulae (I) to (III).

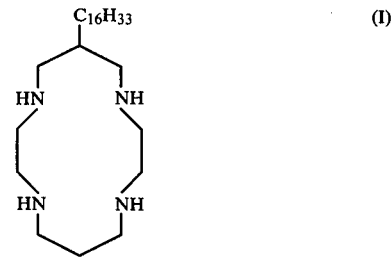

(I)

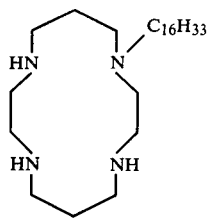

(II)

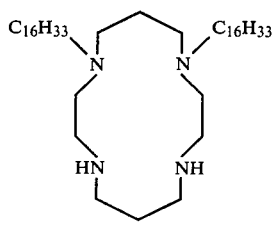

(III)

Hereinafter, a method of synthesizing the alkyl cyclam of the present invention will be explained. Though alkyl cyclam can be synthesized by various methods, the typical method will be explained in more detail.

Diethyl malonate represented by the formula:

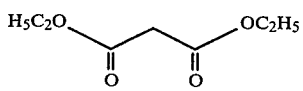

and 1,4,8,11-tetraazaundecane represented by the formula:

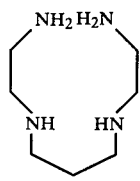

are reacted in ethanol to produce 1,5,8,12-tetraaza-2,4-dioxycyclotetradecane represented by the formula:

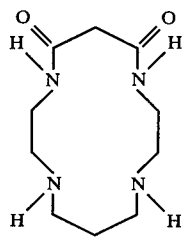

This compound is then reacted with an alkyl halide containing at least 8 carbon atoms whereby alkyl groups are introduced unto one or more nitrogen or carbon atoms. The thus obtained compound is reduced in tetrahydrofuran using a reducing agent such as diborane or the like, whereupon alkyl cyclam of the present invention is obtained.

In accordance with another method of synthesizing alkyl cyclam, active hydrogens of diethyl malonate are previously substituted with alkyl groups containing at least 8 carbon atoms, and the thus obtained compound is reacted with 1,4,8,11-tetraazaundecane or its alkyl substituted compound to obtain an alkyl substituted compound of 1,5,8,12-tetraaza-2,4-dioxycyclotetradecane, which is then subjected to such a reduction reaction as described above. In this case, it is possible, if desired, to suitably increase the number of alkyl groups to be introduced by reacting an alkyl halide containing at least 8 carbon atoms prior to the reduction.

The thus obtained alkyl cyclam of the present invention is oil-soluble, and it captures metal ions in an aqueous solution quantitatively and at high speeds to extract them in an oil layer, showing high selectivity according to the kind of metal.

Removal of metal ions contained in an aqueous solution using the alkyl cyclam of the present invention can be carried out by adding an alkyl cyclam to the aqueous solution to be treated, at room temperature, and then a neutral solvent such as petroleum ether, benzene, chloroform, methylene chloride, ethyl ether, tetrahydrofuran, ethyl acetate and the like is added thereto to extract the alkyl cyclam metal ion complex in the organic solvent layer. For liberating the metal ions from the extracted alkyl cyclam, it is sufficient that an acid is added to the organic solvent and stirring is effected. Therefore, since the alkyl cyclam of the present invention is able to efficiently capture metal ions and at the same time, to easily liberate the metal ions captured, it can be recovered by a simple operation after use and re-used.

As apparent from the above explanation, the alkyl cyclam of the present invention can be employed for processing waste water, recovering specific heavy metals from seawater, and further for separating, purifying and concentrating metals. Hereinafter, the present invention will be explained by reference to the following examples and application examples.

EXAMPLE 1

(1) A mixture of 37.2 grams (0.231 mole) of diethyl malonate and 37.0 grams (0.231 mole) of 1,4,8,11-tetraazaundecane was refluxed in about 1.5 liters of ethanol for 4 days. Thereafter the ethanol was distilled away to adjust the amount to about 500 milliliters and crystals precipitated were recrystallized from ethanol. Thus, 14.9 grams of colorless prism crystals, 1,5,8,12-tetraaza-2,4-dioxycyclotetradecane was obtained. The yield was 28.3%.

(2) A mixture of 10 grams (43.9 millimiles) of the above 1,5,8,12-tetraaza-2,4-dioxycyclotetradecane and 26.7 grams (87.8 millimoles) of cetyl bromide ($C_{16}H_{33}Br$) was refluxed in about 100 milliliters of ethanol overnight, and then allowed to stand at room temperature. The mixture was neutralized with ethanol with caustic soda dissolved therein. Potassium bromide precipitate was separated, and the ethanol was then distilled away. The residue was extracted with methylene chloride, and the resulting extract was shaken with distilled water three times to remove the methylene chloride. Thereafter, it was separated by column chromatography (extraction solvent: chloroform). The thus obtained compound was recrystallized from ethanol, and 7.2 grams of a white spherical solid compound represented by the formula:

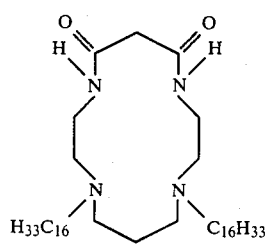

(IV)

was obtained. The yield was 23.3%.

(3) 6.9 grams (10.23 millimoles) of Compound (IV) obtained in the procedure (2) was reduced in 100 milliliters of tetrahydrofuran by the use of 2.51 grams of diborane. Thereafter, the tetrahydrofuran was distilled away, and the residue was refluxed with 6 N hydrochloric acid (containing a small amount of ethanol to prevent foaming) overnight to remove the diborane. The solids precipitated were obtained by filtering and neutralized with ethanol dissolved caustic soda therein. After distilling away the ethanol, the residue was extracted with methylene chloride and shaken with water three times. After drying the methylene chloride layer over Glauber's salt and distilling away the methylene chloride, 4.5 grams of oily or waxy solid alkyl cyclam represented by Formula (III) was obtained. The yield was 70%. The analytical results of this alkyl cyclam were as follows:

Elemental Analysis

| | Calculated (%) | Found (%) |
|---|---|---|
| C | 77.71 | 77.52 |
| H | 13.66 | 13.71 |
| N | 8.63 | 8.77 |

Infrared Analysis (KBr tablet method)

2925 cm$^{-1}$ ($\nu_{as}$ CH$_2$), 2850 cm$^{-1}$ ($\nu_s$ CH$_2$), 2800 cm$^{-1}$ ($\nu_s$ CH$_2$) 1460 cm$^{-1}$ ($\delta$ CH$_2$), 1380 cm$^{-1}$ ($\delta$ CH$_3$), 1300 cm$^{-1}$ ($\delta$ CH$_2$), 1140 cm$^{-1}$ ($\nu$ CN), 1110 cm$^{-1}$ ($\nu$ CN), 1070 cm$^{-1}$ ($\nu$ CN), 720 cm$^{-1}$ ($\delta$ CH$_2$)

NMR Analysis (solvent: CDCl$_3$)

$\delta$ 0.92 ppm (6H), $\delta$ 1.33 ppm (58H), $\delta$ 2.5 ppm (22H)

Others

White waxy solid
Molecular weight 649.12

EXAMPLE 2

A mixture of 7.99 grams (35 millimoles) of 1,5,8,12-tetraaza-2,4-dioxycyclotetradecane obtained in the procedure (1) of Example 1 and 10.7 grams (35 millimoles) of cetyl bromide was refluxed in about 100 milliliters of ethanol overnight. The subsequent operations were conducted in the same manner as in the procedures (2) and (3) of Example 1 with the exception that a mixed solvent of chloroform:ethanol=5:1 was used as an extraction solvent for column chromatography. As a result, 2.71 grams of white spherical solid compound represented by the formula:

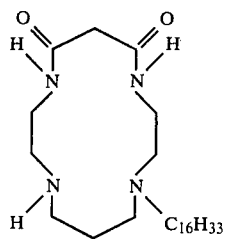

(V)

was obtained. The yield was 17%. On reducing 1.85 grams (4.1 millimoles) of the compound obtained above, 0.6 grams of oily or waxy solid, alkyl cyclam represented by Formula (II) was obtained. The yield was 34.5%. The analytical results of alkyl cyclam were as follows:

Elemental Analysis

| | Calculated (%) | Found (%) |
|---|---|---|
| C | 52.25 | 52.39 |
| H | 10.30 | 9.87 |
| N | 9.38 | 9.08 |

Infrared Analysis (KBr tablet method)

2920 cm$^{-1}$ ($\nu_{as}$ CH$_2$), 2850 cm$^{-1}$ ($\nu_s$ CH$_2$), 2800 cm$^{-1}$ ($\nu_s$ CH$_2$), 1460 cm$^{-1}$ ($\delta$ CH$_2$), 1360 cm$^{-1}$ ($\delta$ CH$_3$), 1300 cm$^{-1}$ ($\delta$ CH$_2$), 1280 cm$^{-1}$ ($\nu$ CN), 1120 cm$^{-1}$ ($\nu$ CN), 1075 cm$^{-1}$ ($\nu$ CN), 720 cm$^{-1}$ ($\delta$ CH$_2$)

NMR Analysis (solvent: D$_2$O)

$\delta$ 0.95 ppm (3H), $\delta$ 1.37 ppm (32H), $\delta$ 3.62 ppm (18H)

Others

White waxy solid
Molecular weight: 424.76

EXAMPLE 3

(1) To about 300 milliliters of dry ethanol was added 2.3 grams (0.1 mole) of sodium, and 16.0 grams (0.1 mole) of diethyl malonate was added dropwise at about 50° C. Then 30.5 grams (0.1 mole) of cetyl bromide was added dropwise, and the resulting mixture was stirred for one night. Thereafter the ethanol was distilled away, and the residue was extracted with methylene chloride. The extract was shaken with water and distilled, and at from 170° to 190° C. (0.55 mmHg), 28.6 grams of the alkyl substituted compounds of diethyl malonate represented by the formula:

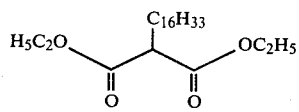

(VI)

was obtained. The yield was 74.5%.

(2) The mixture of 30 grams (78 millimoles) of the compound represented by Formula (VI) obtained by the above procedure (1) and 12.5 grams (78 millimoles) of 1,4,8,11-tetraazaundecane was refluxed in about 500 milliliters of ethanol for four days. Solids precipitated were recrystallized from ethanol, and thus 3.7 grams of white solid compound represented by the formula:

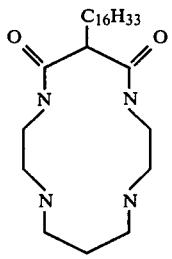

(VII)

The yield was 10.5%.

(3) 1.7 grams (4 millimoles) of the compound represented by Formula (VII) obtained by the procedure (2) was reduced in tetrahydrofuran by the use of diborane, and the subsequent operations were conducted in the same manner as in the procedure (3) of Example 1. After the methylene chloride was distilled away, white solids obtained were recrystallized from ethanol whereby about 600 milligrams of alkyl cyclam represented by Formula (I) was obtained. The yield was 35.3%. The analytical results of this alkyl cyclam were as follows:

Elemental Analysis

|   | Calculated (%) | Found (%) |
|---|---|---|
| C | 73.52 | 73.48 |
| H | 13.29 | 13.76 |
| N | 13.19 | 12.79 |

Infrared Analysis (KBr tablet method)

3260 cm$^{-1}$ ($\nu$ NH), 3180 cm$^{-1}$ ($\nu$ NH), 2920 cm$^{-1}$ ($\nu_{as}$ CH$_2$), 2850 cm$^{-1}$ ($\nu_s$ CH$_2$), 2800 cm$^{-1}$ ($\nu_s$ CH$_2$), 1460 cm$^{-1}$ ($\delta$ CH$_2$), 1330 cm$^{-1}$ ($\delta$ CH$_2$), 1200 cm$^{-1}$ ($\nu$ CN), 1120 cm$^{-1}$ ($\nu$ CN), 1060 cm$^{-1}$ ($\nu$ CN), 965 cm$^{-1}$ ($\delta$ CH$_2$), 820 cm$^{-1}$ ($\delta$ CH$_2$), 720 cm$^{-1}$ ($\delta$ CH$_2$)

NMR Analysis (solvent: CDCl$_3$)

$\delta$ 0.8 ppm (3H), $\delta$ 1.25 ppm (33H), $\delta$ 1.73 ppm (4H), $\delta$ 2.63 ppm (18H)

Others

White solid
Melting point: 115° to 116° C.
Molecular weight: 424.76

Application Example 1

To 5 milliliters of a metal ion-containing aqueous solution (metal ion concentration: $1 \times 10^{-2}$ mole/l) was added 5 milliliters of each of the solutions of alkyl cyclam obtained in Examples 1, 2 and 3, in chloroform (alkyl cyclam concentration: $1.5 \times 10^{-2}$ mole/l) at room temperature. The mixture obtained was shaken for 30 seconds and allowed to stand to separate an aqueous layer from a chloroform layer. A part of the supernatant solution, i.e. the aqueous layer was taken and its metal ion concentration was measured by atomic-absorption spectroscopy. The concentration of uranium ion was measured from the degree of absorption at 430 m$\mu$. The results obtained are shown in Table 1.

Table 1

| | Metal Ions and Their Initial Concentrations | | | | | | | |
|---|---|---|---|---|---|---|---|---|
| | Copper (II)* Ion 635 ppm | | Nickel Ion 587 ppm | | Cobalt Ion 589 ppm | | Uranium Ion 2380 ppm | |
| Alkyl cyclam | A (ppm) | B (%) | A (ppm) | B (%) | A (ppm) | B (%) | A (ppm) | B (%) |
| Compound of Formula (I) | 0.8 | 99.8 | 2.0 | 99.7 | — | — | — | — |
| Compound of Formula (II) | 3.3 | 99.5 | 5 to 8 | 99.0 | 50 | 91.5 | — | — |
| Compound of Formula (III) | 2.2 | 99.7 | 106 | 82.0 | 198 | 66.4 | 714 | 60 |

A: Concentration of remaining metal ions
B: Percentage metal ions captured
*In extracting of copper (II) ion, the pH of the aqueous layer was adusted to 12 by adding 1 or 2 drops of an aqueous concentrated caustic soda solution, and then the separation of the ions was conducted while shaking.

From the results shown in Table 1, it can be seen that all of the alkyl cyclam represented by Formulae (I), (II) and (III) exhibited very high metal ion-capturing efficiencies of more than 99.5%. The values obtained after stirring for 6 hours were substantially the same as the values shown in Table 1. The rate at which the copper (II) ion was captured by alkyl cyclam represented by Formula (III), was measured, and it was found that its half-life period was less than 2 seconds. With alkyl cyclam represented by Formula (I), the same results were obtained. For the cobalt and nickel ions, alkyl cyclam represented by Formulae (II) and (III) did not show so high capturing efficiencies.

On the other hand, the alkyl cyclam represented by Formula (I) quantitatively carried the nickel ion into the chloroform layer at pH 12, although the cobalt ion was left in the aqueous layer as the complex thereof with the alkyl cyclam. At pH 5, the nickel and cobalt ions were present in the aqueous layer as the complexes thereof with the alkyl cyclam.

As described above, the alkyl cyclam of the present invention show marked selectivity according to the kind of metal ions.

Application Example 2

The procedure of Application Example 1 was repeated with the exception that the concentration of the copper (II) ion in an aqueous solution was changed. The results obtained are shown in Table 2. The capturing agent used was alkyl cyclam represented by Formula (III).

Table 2

| Initial Concentration of Copper (II) Ion (ppm) | Concentration of Remaining Copper (II) Ion (ppm) | Metal Ion-capturing Efficiency (%) |
|---|---|---|
| 635 | 2.2 | 99.7 |
| 63.5 | 1.1 | 98.3 |
| 6.35 | 0.13 | 98.0 |

From the results shown in Table 2, it can be seen that alkyl cyclam of the present invention are able to capture efficiently metal ions in markedly low concentrations.

Application Example 3

The procedure of Application Example 1 was repeated several times with the exception that an aqueous solution containing 635 ppm of copper (II) ion was used. The results obtained are shown in Table 3. The capturing agent used was alkyl cyclam represented by Formula (III).

Table 3

| Frequency of Operation Repeated | Concentration of Remaining Copper (II) Ion (ppm) | Metal Ion-capturing Efficiency (%) |
|---|---|---|
| 1 | 2.2 | 99.7 |
| 2 | 0.8 | 99.9 |
| 3 | 0.6 | 99.9 |

What is claimed is:

1. An alkyl cyclam of the formula

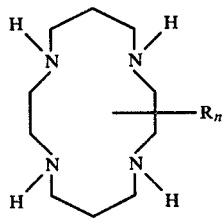

wherein R is an alkyl group having from 8 to 20 carbon atoms and n is 1 or 2,
said alkyl cyclam being selected from the group consisting of the following alkyl cyclams:

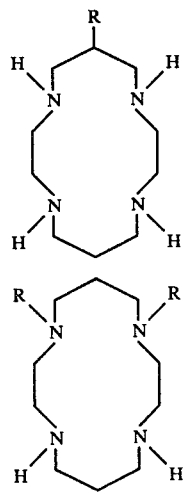

and

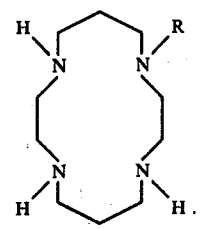

2. The alkyl cyclam of claim 1 of the formula

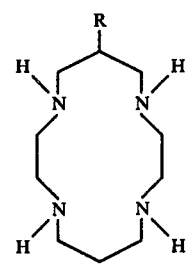

3. The alkyl cyclam of claim 1 of the formula

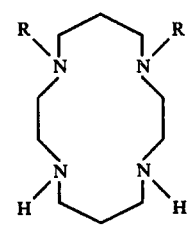

4. The alkyl cyclam of claim 1 of the formula

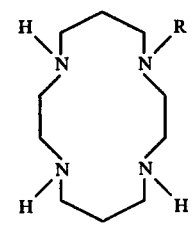

5. The alkyl cyclam of claim 1, wherein the compound is represented by the formula

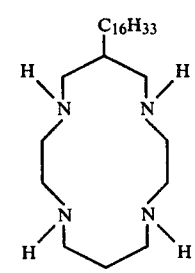

6. The alkyl cyclam of claim 1, wherein the compound is represented by the formula

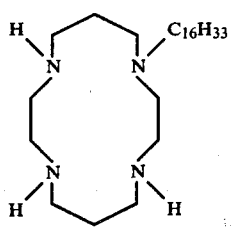
7. The alkyl cyclam of claim 1, wherein the compound is represented by the formula
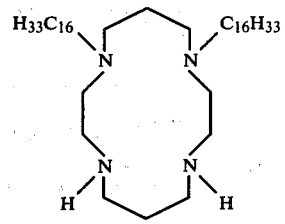
* * * * *